(12) United States Patent
Higazi

(10) Patent No.: US 6,911,316 B1
(45) Date of Patent: Jun. 28, 2005

(54) MEDICAL USES OF SCUPA/SUPAR COMPLEX

(75) Inventor: Abd Al-Roof Higazi, Shimshon (IL)

(73) Assignee: Thrombotech Ltd., Nazareth (IL)

( * ) Notice: Subject to any disclaimer, the term of this patent is extended or adjusted under 35 U.S.C. 154(b) by 0 days.

(21) Appl. No.: 09/325,917

(22) Filed: Jun. 4, 1999

Related U.S. Application Data

(63) Continuation of application No. PCT/IL97/00402, filed on Dec. 9, 1997.
(60) Provisional application No. 60/032,676, filed on Dec. 9, 1996.

(51) Int. Cl.[7] .......................... C12Q 1/56; C12Q 1/00; G01N 33/53; G01N 33/567; G01N 33/543
(52) U.S. Cl. .......................... 435/13; 435/4; 435/7.1; 435/7.21; 435/7.91; 435/7.92; 436/86; 436/536; 436/512; 436/513; 530/350; 530/380; 530/300; 530/385; 530/386; 530/387.1; 514/1; 514/2; 514/14
(58) Field of Search ...................... 514/1, 2, 14; 435/4, 435/7.1, 7.21, 7.91, 7.92, 13; 530/350, 380, 385, 386, 387.1, 300; 436/86, 536, 512, 513

(56) References Cited

U.S. PATENT DOCUMENTS

| | | | |
|---|---|---|---|
| 5,455,044 A | 10/1995 | Kim et al. | 424/450 |
| 5,558,852 A | 9/1996 | Bigner et al. | 424/1.49 |

OTHER PUBLICATIONS

Harlow and Lane. Antibodies, A Laboratory Manual, Chapter 59:96–99, 1988.*
Lindahl, T.L. et al., "The mechanism of the reaction between human plasminogen–activator inhibitor 1 and tissue plasminogen activator," Biochem. J. 265(1):109–113 (1990).
Ploug, M. et al., "Ligand Interaction between Urokinase-Type Plasminogen Activator and Its Receptor Probed with 8–Anilino–1–naphthalenesulfonate. Evidence for a Hydrophobic Binding Site Exposed Only on the Intact Receptor," Biochemistry, 33:8991–8997 (1994).
Pannell; R. et al., "Activation of Plasminogen by Single–Chain Urokinase or by Two–Chain Urokinase—A Demonstration That Single–Chain Urokinase Has a Low Catalytic Activity (Pro–Urokinase)," Blood, 69(1):22–26 (1987).
Collen, D., "On the Regulation and Control of Fibrinolysis," Thrombosis and Haemostasis, 43(2):77–89 (1980).
Lijnen, H.R. et al., "The Mechanism of Plasminogen Activation and Fibrin Dissolution by Single Chain Urokinase-Type Plasminogen Activator in a Plasma Milieu In Vitro," Blood, 73(7):1864–1872 (1989).
Wang, J. et al., "Plasminogen activation by pro–urokinase in complex with its receptor Dependence on a tripeptide (Spectrozyme plasmin)," Eur. J. Biochem. 247(1):256–261 (1997).

Behrendt, N. et al., "Reply to comment on 'Effect of purified, soluble urokinase receptor on the plasminogen-prourokinase activation system' (A.A–R. Higazi)," FEBS Letters 402:293–294 (1997).
Deutsch, D.G. et al., "Plasminogen: Purification from Human Plasma by Affinity Chromatography," Science, 170(3962):1095–1096 (1970).
Kasai, S. et al., "Primary Structure of Single–chain Pro–urokinase," J. Biol. Chem., 260(22):12382–12389 (1985).
Ellis, V. et al., "Inhibition of Receptor–bound Urokinase by Plasminogen–activator Inhibitors," J. Biol. Chem., 265(17):9904–9908 (1990).
Ellis, V. et al., "Plasminogen Activation by Receptor–bound Urokinase," J. Biol. Chem., 266(19):12752–12758 (1991).
Schwartz, B.S., "Differential Inhibition of Soluble and Cell Surface Receptor–bound Single chain Urokinase by Plasminogen Activator Inhibitor Type 2," J. Biol. Chem., 269(11):8319–8323 (1994).
Higazi, A.A. et al., "Identification of an Inhibitor of Tissue-type Plasminogen Activator–mediated Fibrinolysis in Human Neutrophils," J. Biol. Chem. 270(16):9472–9477 (1995).
Del Villar, K. et al., "Amino Acid Substitutions That Convert the Protein Substrate Specificity of Farnesyltransferase to That of Geranylgeranyltransferase Type I," J. Biol. Chem., 272(1):680–687 (1997).
Zhang, L. et al., "Regulation of Single Chain Urokinase Binding, Internalization, and Degradation by a Plasminogen Activator Inhibitor 1–Derived Peptide," J. Biol. Chem. 272(43):27053–27057 (1997).
Behrendt, N. et al., "Domain Interplay in the Urokinase Receptor," J. Biol. Chem., 271(37):22885–22894 (1996).
Ellis, V., "Functional Analysis of the Cellular Receptor for Urokinase in Plasminogen Activation," J. Biol. Chem., 271(25):14779–14784 (1996). JBC Online Bio. Mol. pp. 1–13.
Higazi, A.A. et al., "Regulation of fibrinolysis by non–esterified fatty acids," Biochem J., 300:251–255 (1994).
Higazi, A.A. et al., "Regulation of Single Chain Urokinase by Small Peptides," Thromb. Res. 84(4):243–252 (1996).
Higazi, A.A. et al., "Enhancement of the Enzymatic Activity of Single–chain Urokinase Plasminogen Activator by Soluble Urokinase Receptor," J. Biol. Chem. 270(29):17375–17380 (1995).
Higazi, A.A. et al., "Unesterified Long Chain Fatty Acids Inhibit the Binding of Single Chain Urokinase to the Urokinase Receptor," Biochemistry, 35(21):6884–6890 (1996).

(Continued)

Primary Examiner—Alana M. Harris

(57) ABSTRACT

Methods of using a complex (scuPA/suPAR) which has thrombolytic activity under physiological conditions and in the presence of IgG, or of at least one IgG-derived peptide, which complex comprises a single chain urokinase type plasminogen activator (scuPA) and a soluble urokinase plasminogen activator receptor (suPAR), for the treatment and/or prevention of thromboembolic disorders associated with the formation of fibrin clots are disclosed.

12 Claims, 16 Drawing Sheets

OTHER PUBLICATIONS

Higazi, A.A. et al., "Interaction of Single–Chain Urokinase With Its Receptor Induces the Appearance and Disappearance of Binding Epitopes Within the Resultant Complex for Other Cell Surface Proteins." *Blood,* 88(2):542–551 (1996).

Higazi, A.A. et al., "Single Chain Urokinase–Type Plasminogen Activator Bound To Its Receptor Is Relatively Resistant To Plasminogen Activator Inhibitor Type 1," *Blood,* 87(9):3545–3549 (1996).

Higazi, A.A. et al., "Lysis of Plasma Clots by Urokinase-Soluble Urokinase Receptor Complexes," *Blood,* 92(6):2075–2083(1998).

Higazi, A.A. et al., "Soluble Human Urokinase Receptor Is Composed of Two Active Units," *J. Biol. Chem.,* 272(8):5348–5353 (1997).

Higazi, A.A., "Commentary on: 'Effect of purified soluble urokinase receptor on the plasminogen prourokinase activation system' by N. Behrendt and K. Dano, *FEBS Letters, 393* (1996) 31–36", *FEBS Letters 402*:291–292 (1997).

Behrendt, N., et al., "The Structure and Function of the Urokinase Receptor, a Membrane Protein Governing Plasminogen Activation on the Cell Surface," *Biol. Chem. Hoppe–Seyler 376*:269–279 (1995).

* cited by examiner

SEQUENCE LISTING

<160> NUMBER OF SEQ ID NOS: 5

<210> SEQ ID NO 1
<211> LENGTH: 12
<212> TYPE: PRT
<213> ORGANISM: unknown
<220> FEATURE:
<223> OTHER INFORMATION: homo sapien
<221> NAME/KEY: VARIANT
<222> LOCATION: (1)...(12)
<223> OTHER INFORMATION: Xaa = Any Amino Acid

<400> SEQUENCE: 1

Glu Ile Val Met Thr Gln Ser Pro Xaa Thr Leu Ser

-continued

```
<210> SEQ ID NO 2
<211> LENGTH: 17
<212> TYPE: PRT
<213> ORGANISM: unknown
<220> FEATURE:
<223> OTHER INFORMATION: homo sapien
<221> NAME/KEY: VARIANT
<222> LOCATION: (1)...(17)
<223> OTHER INFORMATION: Xaa = Any Amino Acid

<400> SEQUENCE: 2

Glu Val Gln Leu Val Glu Ser Gly Gly Xaa Leu Val Gln Pro Gly Xaa
 1               5                  10                  15

Ser

<210> SEQ ID NO 3
<211> LENGTH: 18
<212> TYPE: PRT
<213> ORGANISM: unknown
<220> FEATURE:
<223> OTHER INFORMATION: homo sapien
<221> NAME/KEY: VARIANT
<222> LOCATION: (1)...(18)
<223> OTHER INFORMATION: Xaa = Any Amino Acid

<400> SEQUENCE: 3

Glu Val Gln Leu Val Glu Ser Gly Gly Xaa Leu Val Gln Pro Gly Arg
 1               5                  10                  15

Glu Ser

<210> SEQ ID NO 4
<211> LENGTH: 20
<212> TYPE: PRT
<213> ORGANISM: unknown
<220> FEATURE:
<223> OTHER INFORMATION: homo sapien

<400> SEQUENCE: 4

Glu Ile Val Met Thr Gln Ser Pro Val Thr Leu Ser Val Ser Pro Gly
 1               5                  10                  15

Glu Arg Ala Thr
         20

<210> SEQ ID NO 5
<211> LENGTH: 20
<212> TYPE: PRT
<213> ORGANISM: unknown
<220> FEATURE:
<223> OTHER INFORMATION: homo sapien

<400> SEQUENCE: 5

Glu Val Gln Leu Val Glu Ser Gly Gly Asp Leu Val Gln Pro Gly Arg
 1               5                  10                  15

Ser Leu Arg Leu
         20
```

MEDICAL USES OF SCUPA/SUPAR COMPLEX

This application is a continuation and claims priority to International Application PCT/IL97/00402, filed Dec. 9, 1997 and Provisional Application No. 60/032,676, filed Dec. 9, 1996.

FIELD OF THE INVENTION

The present invention relates to a novel use of a complex (scuPA/suPAR as hereafter defied) which comprises a single chain urokinase type plasminogen activator (scuPA) and a soluble urokinase plasminogen activator receptor (suPAR), in the preparation of pharmaceutical compositions for the treatment and/or prevention of thromboembolic disorders associated with the formation of blood clots.

BACKGROUND OF THE INVENTION

Plasminogen activators are widely used in the treatment of thromboembolic diseases. One of these activators is urokinase plasminogen activator (uPA), known to be synthesized as a proenzyrne consisting of a single-chain protein (scuPA) [Pannell, R. & Gurewich, V., Blood 69:22–28 (1987)].

Limited proteolysis of scuPA results in the formation of two chains (tcuPA), considered to be the active form of the enzyme [Kasai. S., et al. J. Biol. Chem. 260:12382–12389 (1985)]. One of the most important regulators of uPA is the plasminogen activator inhibitor-1 (PAI-1). This regulator interacts with tcuPA in a very rapid two-step reaction, leading to the formation of an inactive, SDS-stable 1/1 complex [Lindahl, T. L., et al., Biochem. J. 265:109–113 (1990)]. The binding of tcuPA to UPAR only slightly reduces the susceptibility of tcuPA to the inhibitory effect of PAI-1 [Ellis, V., etal., J. Biol. Chem. 265:9904–9908 (1990)].

More recent reports by the inventor have shown that the proenzyme (scuPA) can be activated by an alternative mechanism. Binding of scuPA to a soluble form of the urokinase plasminogen activator receptor (suPAR) leads to activation of the enzyme without prior cleavage [Higazi, A A-R., et al., J. Biol. Chem. 270:17375–17380 (1995)]. Single-chain urokinase plasminogen activator (scuPA) is the unique form of urokinase secreted by cells. ScuPA has low intrinsic activity, but cleavage of a single peptide bond leads to the formation of the active, two-chain urokinase plasminogen activator (tcuPA). The activity of the scuPA/suPAR complex is relatively resistant to PAI-1. The mechanism of PAI-1 inhibition of the scuPA/suPAR complex is competitive and reversible [Higazi, A A-R., et al., Blood 87:3545–3549 (1996)]. Resistance of the scuPA/suPAR complex to other inhibitors, such as PAI-2, has also been described [Schwartz, B. S., J. Biol. Chem. 269:8319–8323 (1994)]. Evidently, when the two forms of an enzyme are fully active, the susceptibility to the effects of regulators present in the physiological environment will determine which is the active or "more active" form. The fact that the activity of the scuPA/suPAR complex is similar to that of tcuPA, whereas its sensitivity to inhibition is lower, led to the finding that under physiological conditions the complex is the active form of urokinase, which underlies the present invention.

The opinion was that tcuPA is the physiological urokinase plasminogen activator whereas scuPA serves as the proenzyme. This concept was based on the greater catalytic activity of tcuPA, as compared to scuPA. To the contrary, more recent studies have provided evidence that the activity of scuPA, bound to its receptor, suPAR, is in the same range as that of tcuPA [Higazi, A A-R., (1995) ibid.; Higazi, A A-R. et al. (1996) ibid.]. On the other hand, Behrendt et al. and Ellis et al. [Behrendt N., et al., Biol. Chem. 376:259–279 (1995); Ellis V., J. Biol. Chem. 271:14779–14784 (1996)] described suPAR as having no stimulatory effect on scuPA activity. However, a more recent publication [Behrendt N. & Dano K, FEBS Lett. 339:31–36 (1996)] describes a stimulatory effect of suPAR on scuPA activity, but the mechanism of this stimulation was questioned [Higazi, A A-R, FEBS Lett 402:291–292 (1997)].

Some of the conflicting results probably stemmed from different experimental conditions and chromogenic substrates of plasmin. The inventor found that when using the physiological substrate of the fibrinolytic system, i.e. human plasma clots, suPAR stimulated the intrinsic activity of scuPA. Using a plasma-derived clot as a substrate of the fibrinolytic system, the activity of the scuPA/suPAR complex was significantly greater than that of tcuPA. On the other hand, suPAR inhibited the scuPA-mediated fibrinolytic activity when the clot was prepared with purified fibrinogen. Addition of serum to purified fibrinogen resulted in stimulation of suPAR/scuPA-mediated fibrinolysis. It was therefore concluded that activation or inhibition of scuPA activity by suPAR depends on the substrate used. For example, with H-D-norleucyl-hexahydrotyrosyl-lysine-p-nitroanilide D-lactate salt (Spect PL), suPAR stimulated scuPA activity, whereas suPAR was found to inhibit scuPA-mediated plasminogen activation when the activin, of the generated plasmin was determined with a synthetic plasmin substrate H-D-val-leu-lys-p-nitroanilide (S-2251) [Higazi, A A-R., Thromb. Res. 84:243–252 (1996)]. As noted above, it has been suggested that under physiological conditions the complex is the active form of urokinase. Since it appeared that the regulation of scuPA activity by suPAR depends on the nature of the substrate used, the inventor proceeded to examine the suitability of the physiological substrate of the fibrinolytic system, i.e. the plasma clot.

As will be shown hereinafter, suPAR stimulated the activity mediated by scuPA on a clot generated by the coagulation of human plasma. Using a plasma-derived clot as substrate of the fibrinolytic system, the activity of the scuPA/suPAR complex was significantly greater than that of tcuPA. It will further be shown that the effect of serum depends on the presence of intact suPAR. Optimal stimulation of scuPA/suPAR-mediated fibrinolysis will be obtained when serun is incorporated into a clot during the coagulation process.

Therefore, one aim of the present invention is to provide a scuPA/suPAR complex that acts as a plasminogen activator in combination or in the presence of a specific factor that stimulates the fibrinolytic activity of the scuPA/suPAR complex. While searching for such specific factor, the inventor has surprisingly found that it is human IgG protein or an IgG derived peptidewhich have the stimulating effect on the activity of the complex.

SUMMARY OF THE INVENTION

The present invention relates to use of a complex (scuPA/suPAR) which has a thrombolytic activity under physiological conditions and in the presence of IgG or an IgG-derived peptide, which complex comprises a single chain urokinase type plasminogen activator (scuPA) and a soluble urokinase plasminogen activator receptor (suPAR), in the preparation of a thrombolytic pharmaceutical composition for the treatment and/or prevention of a thromboembolic disorder associated with the formation of fibrin clots said complex induced fibrinolysis of said clots. Examples of thromboembolic disorders that may be treated or prevented by said use of the complex of the invention are myocardial infractions, cerebro-vascular events, pulmonary embolism or deep vain thrombosis.

Further the invention is concerned with a thrombolytic pharmaceutical composition for the treatment and/or prevention of a thromboembolic disorder associated with the formation of fibrin clots comprising as active ingredient a therapeutically or preventive effective amount of a complex (scuPA/suPAR) comprising a single chain urokinase type plasminogen activator (scuPA) and a soluble urokinase plasminogen activator receptor (suPAR), which complex can directly or indirectly induce the fibrinolysis of said clots under physiological conditions and in the presence of human IgG or of at least one human IgG-derived peptide.

DETAILED DESCRIPTION OF THE INVENTION

Figure 1A:
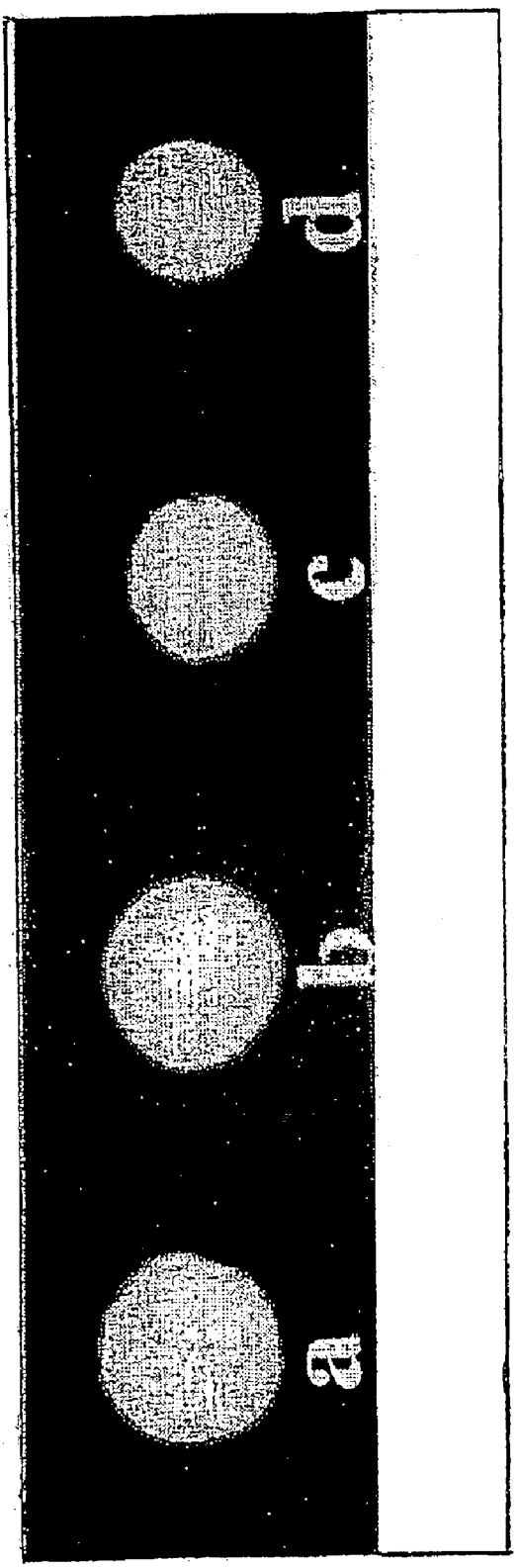
FIG. 1 The effect of suPAR on scuPA-mediated fibrinolysis (purified bovine fibrinogen clot)
(A) ScuPA alone was added to wells (a) and (b); scuPA and suPAR were added to wells (c) and (d). The lytic areas in wells (a) and (b) were 1.60 and 1.63 $cm^2$, respectively; the corresponding areas in wells (c) and (d) were 1.19 and 1.05 $cm^2$, respectively.
(B) ScuPA (open bar) or scuPA/suPAR complex (closed bar) were added to $^{125}I$ radiolabeled fibrinogen clots. After 2 hrs of incubation the fibrinolytic activity (F.A. (cpm)) was determined by measuring the solubilized radioactivity.

The present invention relates to the use of a complex (scuPA/suPAR) which has a thrombolytic activity under physiological conditions and in the presence of IgG or of at least one IgG-derived peptide, which complex comprises a single chain urokinase type plasminogen activator (scuPA) and a soluble urokinase plasminogen activator receptor (suPAR), in the preparation of a thrombolytic pharmaceutical composition for the treatment and/or prevention of a thromboembolic disorder associated with the formation of fibrin clots. The complex scuPA/suPAR is believed to directly or indirectly induce fibrinolysis of plasma derived clots.

By fibrin clot is meant the conversion of fibrinogen to fibrin, whereby red blood cells and other formed elements are entrapped within the coagulated plasma. The enzyme catalyzing this conversion is known to be the thrombin which is formed in shed blood and converts fibrinogen into fibrin, thereby producing fibrin clots by a hydrolyzing action.

Of particular interest is the use of a scuPA/suPAR complex which has a fibrin-specific thrombolytic activity under physiological conditions.

The thromboembolic disorders against which use of the complex is of particular importance are mainly those associated with the formation of fibrin clots, Examples of such disorders are myocardial infractions, cerebro-vascular events, pulmonary embolism, deep vein thrombosis. Evidently, any other disorder associated with the damaging formation of fibrin clots may also be treated or prevented by use of the complex of the present invention.

As will be shown in the following Examples, the surprising thrombolytic activity of the scuPA/suPAR complex, in the presence of plasma-derived clots was examined in comparison to that of equimolar concentrations of scuPA alone or tcuPA alone and is found to be markedly greater than that of scuPA alone or tcuPA alone. While similar results have previously been demonstrated, only with the synthetic low molecular weight plasmin substrate Spect PL [Higazi A A-R. et al. (1995) ibid.; Higazi A A-R. et al. (1996) ibid.; Higazi A A-R & Cines D.B. (1996) ibid.], they did not teach the fibrinolytic activity of the complex on plasma derived clots, i.e under physiological conditions. Furthermore, when a clot produced from purified fibrinogen was used as substrate of the fibrinolytic system, suPAR inhibited the activity of scuPA. These results are similar to the results obtained with another synthetic plasmin substrate, S-2251, that were ascribed to inhibition by suPAR of scuPA activation by plasmin [Higazi, A A-R. & Cines D.B. (1996) ibid.]. The surprising conclusion derived from these studies and from the ones described in detail hereinafter in the Examples is that suPAR can stimulate or inhibit scuPA-mediated plasminogen activation, depending on the type of clot and other conditions.

The major question raised by the stimulatory effect of suPAR on scuPA activity concerns the possibility that the observed stimulation is due to activation by cleavage of scuPA into the two-chain activator, tcuPA. The following Examples show that the stimulator effect of suPAR on scuPA activity, using a plasma-derived clot as substrate of the fibrinolytic system, cannot be attributed to the conversion of scuPA to tcuPA. This conclusion is based on the following observations:

(i) The stimulatory effect of suPAR is inhibited by ATF. as illustrated in FIG. 3.

Figure 4:
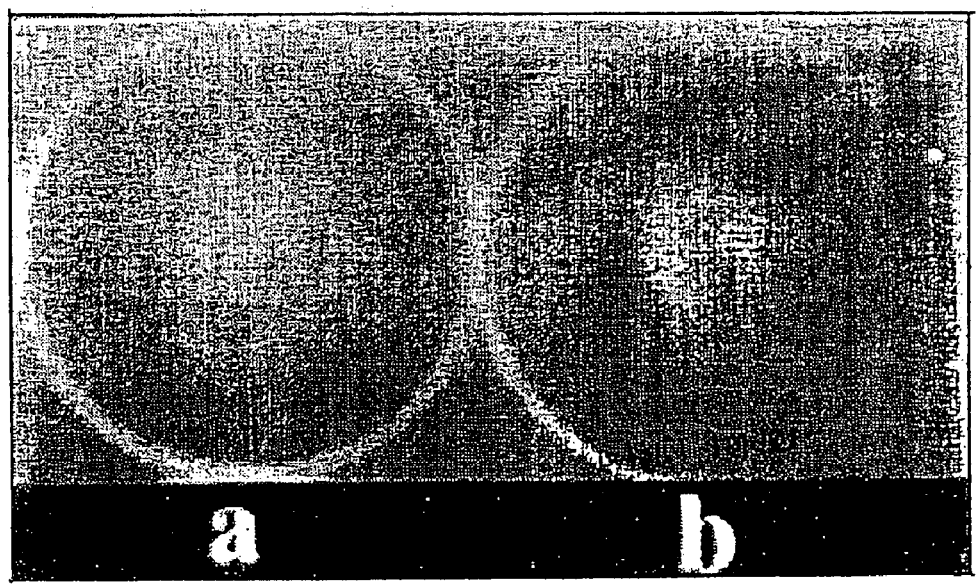
FIG. 4 The effect of suPAR on LMW-scuPA mediated fibrinolysis plasma clot)
Lane (a) LMW-scuPA; lane (b) LMW-scuPA+suPAR FIG. 5 The effect of suPAR on scuPA mediated fibrinolysis (bovine fibrinogen clot reconstituted in serum)
Lane (a) scuPA; lane (b) scuPA+an equimolar concentration of suPAR; lane (c) scuPA+an equimolar concentration of suPAR+50M of ATF.

(ii) The activity or low molecular weight scuPA (LMW-scuPA) is not stimulated by suPAR. as illustrated in FIG. 4.

Figure 8:
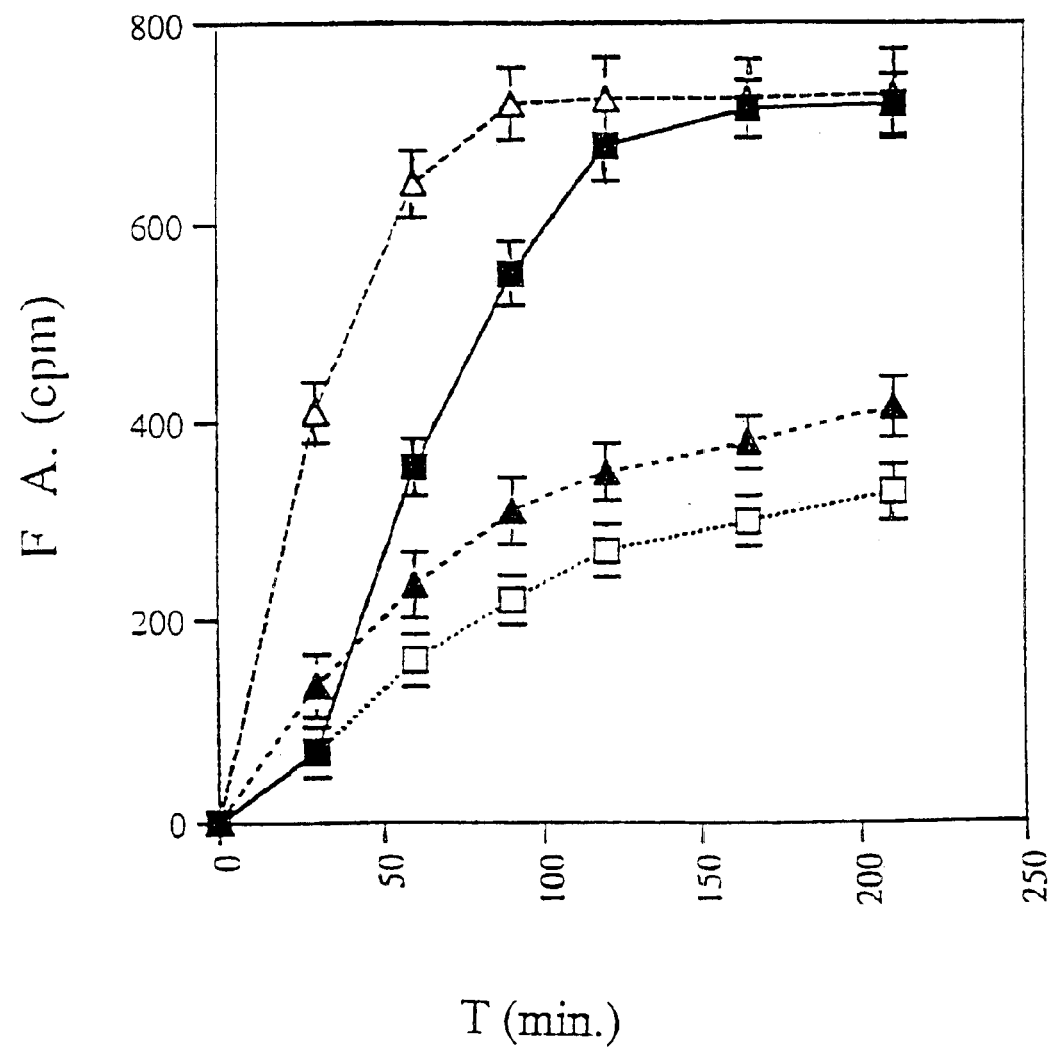
FIG. 8 Comparison between fibrinolysis mediated by tcuPA and by scuPAI/uPAR complex
ScuPA/suPAR complex (■), tcuPA/suPAR complex (Δ) or tcuPA (□) were used as plasminogen activators on a plasma derived clot covered by serum; tcuPA mediated fibrinolysis was also assayed on a fibrinogen derived clot, covered with PBS (Δ).

(iii) The activity of the complex is significantly greater than that of tcuPA alone, as illustrated in FIG. 8.

(iv) The negative effect of suPAR on the activation of scuPA by plasmin [Higazi, A A-R et al. (1996) ibid.; Ellis V. & Behrendt N., J. Biol. Chem. 266:12752–12758 (1991)] would have been expected to result in lower thrombolytic activity of the scuPA/suPAR complex, compared to tcuPA (as shown by the effect of suPAR on scuPA activity in a fibrinogen-derived clot). In contrast, in reality the opposite effect is observed (FIGS. 5–8).

Figure 6:
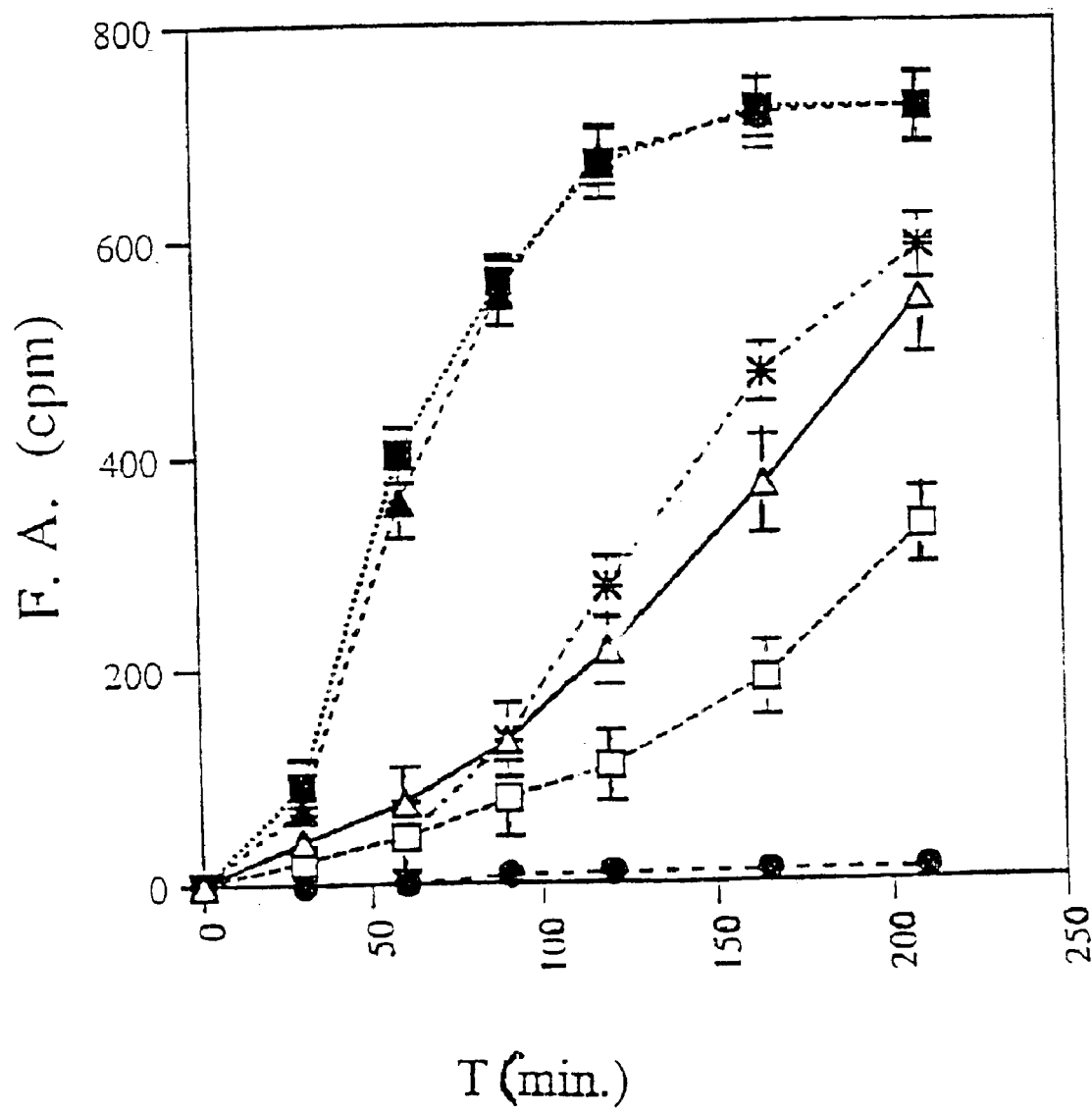
FIG. 6 Effect of suPAR on scuPA activity in aplasma-derived clot ScuPA (25 nM) activity was measured using a radiolabeled plasma-derived clot in the presence (closed symbols) or absence (open symbols) of equimolar concentrations of suPAR. The clots were covered with serum (□) or PBS (Δ). The activity of the scuPA/suPAR complex in the presence of serum and 250 nM ATF (×) or SuPAR alone (•). The plasminogen activator was added to serum or PBS that covered the clot.

(v) The presence of $\alpha_2$-antiplasmin in the plasma-derived clot would have been expected to reduce conversion of scuPA to tcuPA (as observed when scuPA alone was used), rather than result in a significantly increased activity of the scuPA/ suPAR complex, compared to that of the tcuPA (FIGS. 6 and 8). In contrast, the activity of the complex did increase.

Therefore, it was suggested that the activity of the scuPA/suPAR complex should be ascribed to a mechanism different from cleavage of scuPA into tcuPA.

Still, since plasma-derived clots contain endocenous inhibitors of the fibrinolytic system, such as PAI-1 and α2-antiplasmin [Collen. D. Thromb. Haemostasis 43: 77–89 (1980)] and in view of the fact that activity of the scu?A/suPAR complex in the presence of such plasma-derived clots was greater than its activity on a fibrinogen clot devoid of any inhibitor, the inventor assumed that the plasma clot contains a positive regulator of the activity of the complex.

It has now surprisingly been found that a positive regulator of the thrombolytic activity of the scuPA/suPAR complex can be attributed to IgC or to at least one functionally active IgG derived peptide.

The incapability of suPAR fragments DI and DII–III, that bind to and activate scuPA [Hgazi, A A-R, et al., J. Biol. Chem. 272:5348–5353 (1997)], to affect the activity of scuPA, suggests that the IgG present in serum or IgG-derived peptide/s capable of specifically binding to said complex, thereby inducing and/or regulating its fibrinolytic activity, exerts its effect by binding to the suPAR side of the complex and that this binding depends on an intact structure of suPAR. Optimal binding of uPA to suPAR is similar [Higazi, A A-R et at. (1997) ibid.; Ploug M., et al., Biochemistry 33:8991–8997 (1994); Behrendt N., et al., J. Biol. Chem. 271:22885–22894 (1996)].

The IgG protein or any suitable functionally active IgG-derived peptide/s, capable of binding to the complex, probably stimulate the activity of the scuPA/suPAR complex by its presence in the clot or in the liquid phase surrounding it Nevertheless, as will be presented in the following Examples, an optimal effect was obtained when serum was present at the time of clot formation.

The present invention is also concerned with pharmaceutical compositions and in particular with thrombolytic pharmaceutical compositions for the treatment and/or prevention of a thromboembolic disorder associated with the formation of fibrin clots comprising as active ingredient a therapeutically or preventive effective amount of a complex (scuPA/suPAR) comprising a single chain urokinase type plasminogen activator (scuPA) and a soluble urokinase plasminogen activator receptor (suPAR). The complex is capable, directly or indirectly, of inducing fibrinolysis of said clots under physiological conditions and in the presence of IgG or at least one thrombolytically active IgG-derived peptide. As shown in the following Examples, human IgG or human IgG derived peptide/s act as a regulating agent, which regulate the fibrinolytic activity of the scuPA/suPAR complex.

As described hereafter, the pharmaceutical compositions of the invention can be specifically used for the treatment and/or prevention of thromboembolic disorders associated with the formation of fibrin clots. Examples for such are myocardial infractions, cerebro-vascular events, pulmonary embolism or deep vein thrombosis. However, the compositions of the invention may be used for the treatment and/or prevention of any other thromboembolic disorder associated with the formation of plasma clots.

The pharmaceutical compositions of the invention may optionally further comprise human IgG or at least one IgG-derived peptide which specifically binds to the scuPA/suPAR complex. This IgG or peptides derived therefrom are capable of regulating the fibrinolytic activity of said complex.

According to one embodiment of the invention said at least one IgG-derived peptide comprises an amino acid sequence substantially corresponding to the kappa V-III region of the light chain of human IgG. More specifically, the peptide may comprise the sequence EIVMTQSPXTLS (SEQ ID NO:1)or to functional homologues thereof. This sequence which has now been identified by the inventor, as described in detail in Example 5, corresponds to the kappa V-III region of human IgG.

In a second embodiment, the at least one IgG-derived peptide comprises an amino acid sequence substantially corresponding to the V-III region of the heavy chain of human IgG. In particular, the peptide comprises the amino acid sequence EVQLVESGGXLVQPGXS (SEQ ID NO:2) or functional homologues thereof and corresponds to the said V-III region of the heavy chain of human IgG (Example 5).

In a different aspect, the invention relates to a method of treating and/or preventing a thromboembolic disorder associated with the formation of fibrin clots, in a patient in need of such treatment, by administering to said patient a therapeutically effective amount of a complex comprising a single chain urokinase type plasminogen activator (scuPA) and a soluble urokinase plasminogen activator receptor (suPAR), or of the pharmaceutical composition of the invention. In particular, the method may be for treatment and/or prevention of myocardial infractions, cerebro-vascular events, pulmonary embolism or deep vain thrombosis.

The scuPA/suPAR complex or the composition of the invention is administered and dosed in accordance with good medical practice, taking into account the clinical condition of the individual patient, the site and method of administration, scheduling of administration, patient's age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art. The doses may be single doses or multiple doses over a period of several days, but single doses are preferred.

The scuPA/suPAR complex or the pharmaceutical composition of the invention can be administered in various ways and may comprise, in addition to the active ingredient, pharmaceutically acceptable carriers, diluents, adjuncts, preserving agents and vehicles. The pharmaceutical compositions can be administered subcutaneously or parenterally including intravenous, intraarterial, intramuscular, and intraperitoneal administration, as well as intrathecal techniques. Implants of the pharmaceutical preparations may also be useful. The pharmaceutically acceptable carriers, diluents, adjuncts and vehicles as well as implant carriers generally refer to inert, non-toxic solid or liquid fillers, diluents, or encapsulating material not reacting with the active ingredients of the invention.

When administering the complex or the pharmaceutical composition of the invention parenterally, it will generally be formulated in a unit dosage injectable form (solution, suspension, emulsion). The pharmaceutical formulations suitable for injection include sterile aqueous solutions and sterile powders for reconstitution into sterile injectable solutions. The carrier can be any physiologically acceptable suitable carrier, for example, water, or aqueous buffer solutions.

Proper fluidity can be maintained, for example, by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil or peanut oil and esters, such as isopropyl myristate, may also be used as solvent systems for compound compositions.

In addition, various additives which enhance the stability, sterility and isotonicity of the compositions, including antimicrobial preservatives, antioxidants, chelating agents and buffers can be added. Prevention of the action of microorganisms can be ensured by various antibacterial and antifungal agents, for example, parabens, chlorobutanol, phenol, sorbic acid and the like. In many cases it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, any vehicle, diluent, or additive used would have to be compatible with the compositions.

Sterile injectable solutions can be prepared by incorporating the compositions utilized in practicing the present invention in the required amount of the appropriate solvent with various of the other ingredients, as desired.

Nonetheless, the composition disclosed herein in detail can be administered orally to the patient. Conventional forms such as administering the composition as tablets, suspensions, solutions, emulsions, capsules, powders, syrups and the like are usable. Known techniques which deliver it orally or intravenously and retain the biological activity are preferred.

For delivery within the CNS intrathecal delivery can be used with for example an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood brain barrier can be administered. Such formulations can take advantage of methods now available to produce chimeric structures in which the complex of the invention, alone of in combination with human IgG or said IgG-derived peptides are coupled to a brain transport vector thus allowing transportation across the barrier. Further, in appropriate cases blood brain barrier disruption can be utilized.

The invention will now be described in more detail on hand of the following Examples, which are illustrative only and do not limit the scope or the invention, which is defined by the appended claims.

EXAMPLES

Example 1

Materials

ScuPA, suPAR, LMW scuPA, suPAR fiaginents containing domain 1 (DI) or domains 2 and 3 (DII–DIII) and ATF were a gift of Dr. 1. Henkin and Dr. A. Mazar, Abbott Laboratories, Abbott Park Ill. Human fibrinogen and human thrombin were purchased from Sigma. St. Louis, Mo. Bovine fibrinogen was obtained from Calbiochem, Calif. TcuPA was purchased from American Diagnostics, Greenwich, Conn. Plasminogen was prepared as described by Deutsch and Mertz [Deutsch D. & Mertz E.T., Science 170:1095–1096 (1970)]. Plasma was obtained from the Hadassah Hospital blood bank. Blood used to obtain plasma was drawn from healthy volunteers. Blood (450 ml) was collected in bags produced by Travenol Laboratories, Ashdod, Israel, containing 63 ml of CPD solution (containing 1.66 g sodium citrate (hydrous), 61 g dextrose, 206 mg citric acid and 140 mg moon basic sodium phosphate). Plasma was separated by centrifugation.

Example 2

Biological Assays

Effect of suPAR on Fibrinolysis

Fibrinogen containing plasminogen was reconstituted in phosphate buffered saline (PBS), pH 7.4 or in serum to a concentration of 3 mg/ml. Fibrin clots were prepared by the addition of 0.025 NIH units of human thrombin per 30 ml fibrinogen solution. The mixture was decanted onto the lid of a culture dish and incubated for 60 min at room temperature. After clot formation, portions of 10 μl of PBS containing 1 μM scuPA, with or without an equimolar concentration of suPAR, were placed on several parts of the surface of the clot. The clot was incubated for 2 to 3 hr at 37° C., until the appearance of digestion areas on the surface. At that stage the clot was washed several times with PBS and incubated overnight with 0.2° trappan blue. On the following day, the clot was rinsed 4 is times with PBS and photographed The pictures were scanned with a Hoefer GS 300 scanning densitometer. The size of the lytic zones was calculated by the NIH image program.

For some experiments the clot was prepared by the addition of 0.5 NIH units of human thrombin to 30 ml of human plasma and fibrinolysis was induced by addition of scuPA. scuPA/suPARs scuPA/suPAR/ATF, LMW scuPA/suPAR or tcuPA, as indicated in Figures.

Monitoring of Lysis of Radiolebeled Clots

Figure 7:
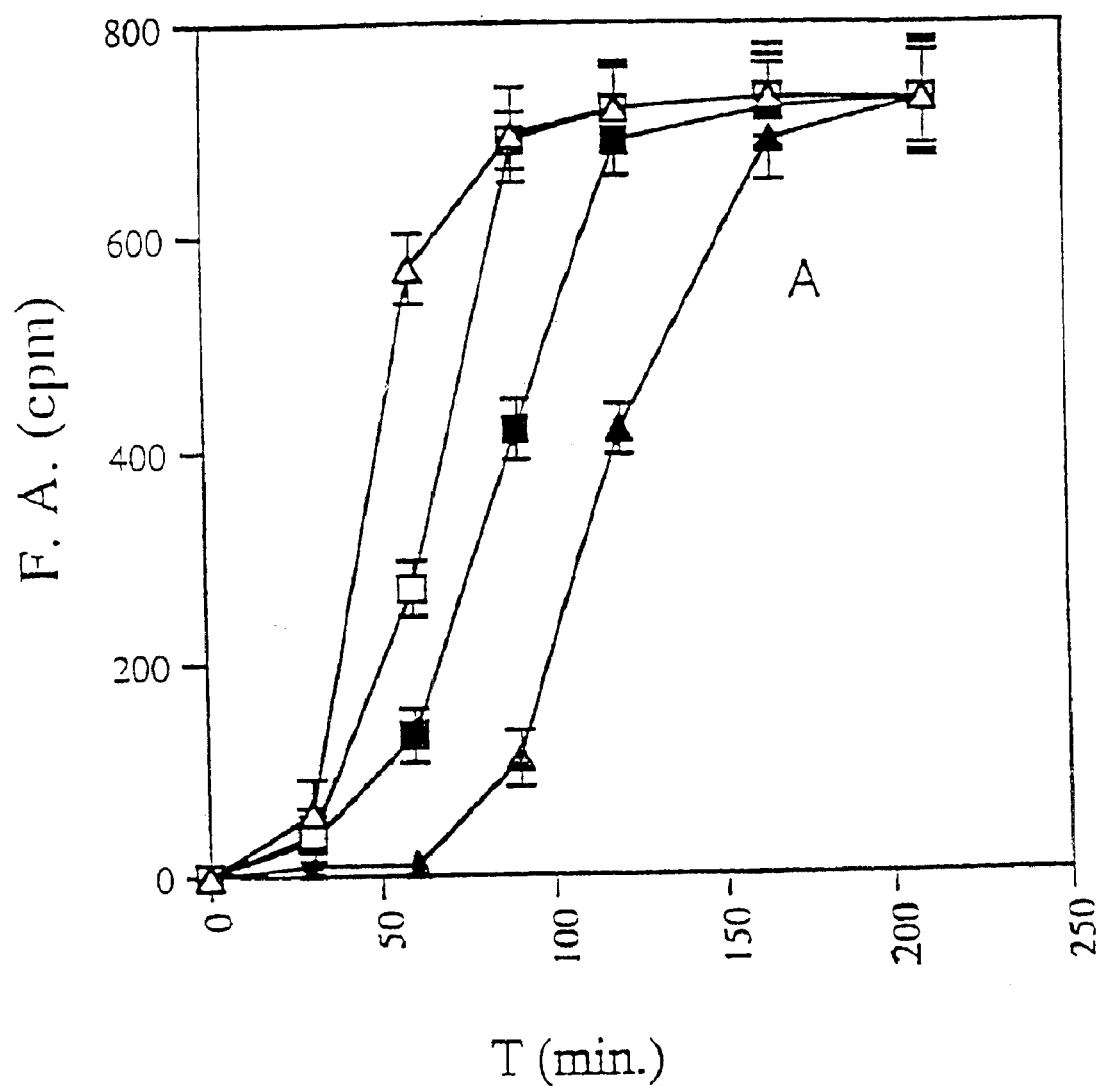
FIG. 7 Effect of sUPAR on scuPA activity on fibrinogen-derived clot
(A) ScuPA mediated fibrinolysis was measured in the presence (closed symbols) or absence (open symbols) of equimolar concentrations of suPAR, using a radiolabeled fibrinogen-derived clot. The clots were covered with serum (□) or PBS (Δ).

Human fibrinogen (Sigma. St. Louis, Mo.) was radiolabeled with $^{125}$I [Higazi, A A-R. & Abu-Much R. et al. J. Biol. Chem. 270:9472–9477 (1995)]. $^{125}$I-labeled fibrinogen was added to a solution of PBS, pH 7.4, containing either 3 mg/ml fibrinogen and 1 μM glu-plasminogen or plasma. Clots were formed in wells of tissue culture plates with an inner diameter of 16 mm (Costar, Cambridge, Mass.). To initiate the clot formation, 10 μl of a solution containing 2 NIH units of thrombin (Sigma. St. Louis, Mo.) were added to 0.4 ml of fibrinogen solution or to plasma. For determination of fibrinolysis, plasminogen activating agents (1 μM) or 1376 MAT cells, in a total volume of 10 μl each, were directly added to the center of the clot and after incubation for specific periods, the wells were washed and the radioactivity of the lavage solution was determined by means of a gamma counter. Fibrinolysis was also measured as previously described [Higazi, A A-R., et al. Biochem. J. 300:251–255 (1994)], by addition of 0.4 ml of serum or PBS, containing 25 nM of the plasminogen activator agent (scuPA, scuPA/suPAR complex or tcuPA). The plates were incubated at 37° C. in an incubator for the required time (about 2 hours, see legends to the Figures). Aliquots of 25 μl were removed at the specific time point for counting of the solubilized label in a gamma counter. Fibrinolytic activity was determined by following the release from the $^{125}$I-labeled fibrin clot of labeled soluble degradation products of fibrin and is illustrated in FIGS. 7 and 8.

All experiments were repeated at least 3 times.

Example 3

Identification of the Activity Regulator

Preparation of suPAR-Sepharose

SUPAR from SP2/0 cells was purified as previously described [Higazi, A A.-R., et al., J. Biol. Chem. 272:680–685 (1997)]. CNBr-Sepharose (Sigma Cat. No. C9142) was swelled in 0.1 mM HCI for 2 hr at room temperature, then washed with 500 ml H$_2$O through a sintered glass funnel, followed by washing with 500 ml of 0.5 M NaHCO$_3$, pH 8.5. In a 50 ml centrifuge tube suPAR (30 ml total in 0.5M NaHCO$_3$, pH 8.5) was added to the CNBr-Sepharose, and the volume was adjusted to 50 ml by adding 0.5 M NaHCO$_3$ pH 8.5. the tube was placed on a rocker platform and incubated at 4° C. for 16 hr. The supermatant was then vacuum aspirated from the suPAR-Sepharose using a sintered glass funnel and the residual suPAR remaining in the supermatant was determined by measuring the absorbance at 280 nm and calculating the concentration using A$_{280}$=0.89 AUrml/mg. the efficiency of coupling was calculated to be >95%. The suPAR-Sepharose was then washed with 1 liter of H$_2$O, followed by 1 liter of 02 M Tris-HCI, pH 8.3. residual CNBr was discharged from the resin by incubating the suPAR-Sepharose in 0.2 M Tris-HCl, pH 8.3, on a rocker platform for 2 hr at room temperature. The resin was loaded into a column (1.5×50 cm$^2$) and the column conditioned by washing sequentially with 10 column volumes of PBS. 10 column volumes of PBS+1 M HCI, 10 column volumes of PBS, 10 column volurnes of 0.2 M glycine, pH 3.0 and finally with PBS sufficient to re-equilibrate the column to pH 7.4.

Isolation of scuPA/suPAR Activity Regulator from Plasma

Figure 10:
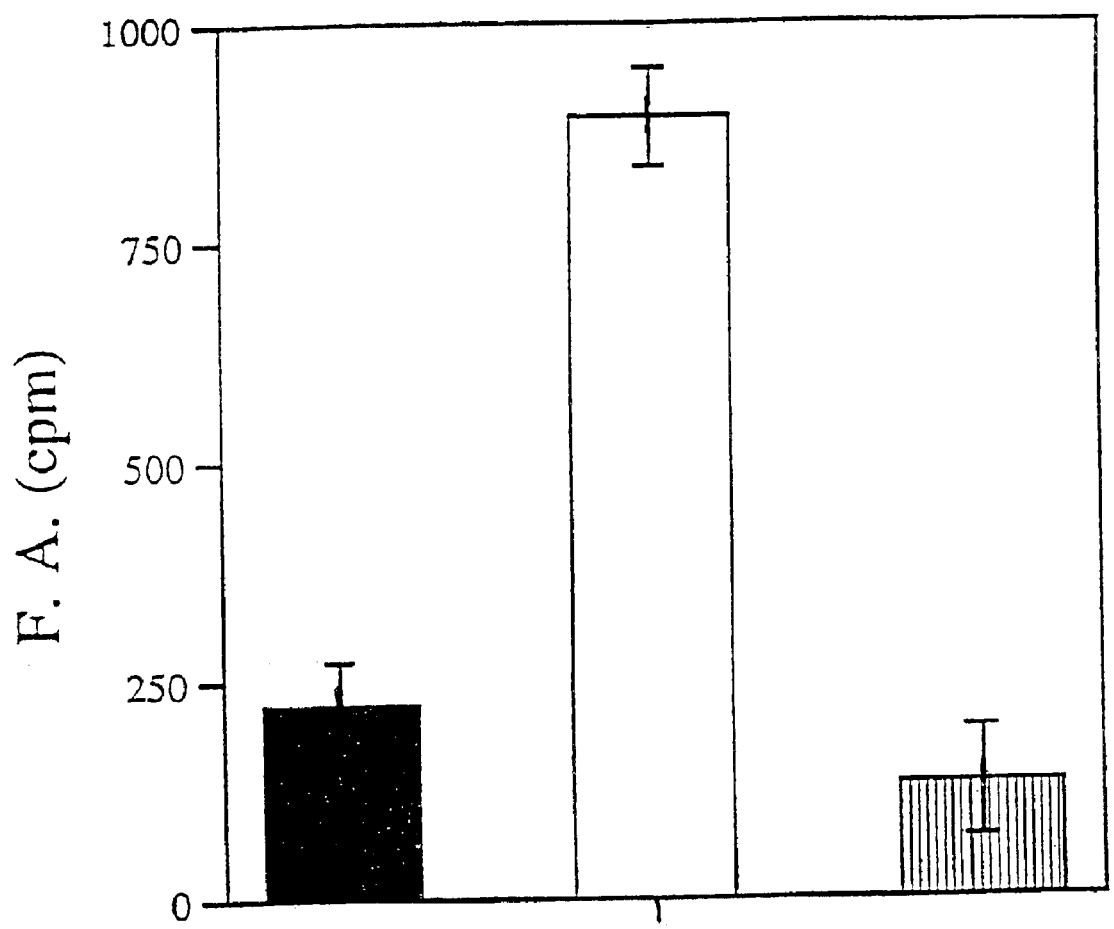
FIG. 10 The effect of plasma-derived regulator on fibrinolysis
The fibrinolytic activity (F.A. (cpm)) of the samples used for SDS-PAGE analysis in FIG. 9 was determined using a fibrinogen-derived clot. ScuPA/suPAR from lane (5) (close bar), scuPA/suPAR and plasma derived proteins from lane (3) (open bar) and suPAR and plasma derived proteins from lane (4) (vertical strips).

SuPAR-Sepharose (1 ml) was incubated for 1 hr at 4° C. with or without 100 nM scuPA. To each of the mixtures, 10 ml of either citrated plasma or PBS were added. After a second incubation period of 1 hr at 4° C. the beads (bound to IgG protein) were isolated by centrifugation and washed 4 times with PBS. A portion of the precipitated was analyzed by SDS-PAGE and another portion was added to a radiolabeled fibrinogen-derived clot containing 1 μM glu-plasminogen. The fibrinolytic activity was determined as described herein before and is illustrated in FIG. 10.

Gel Electrophoresis

Samples containig 10% SDS and Coomassie blue, in a final volume of 50 μl were heated for 2 min in a boiling water bath. Aliquots of 25 μl were applied onto 12% SDS-15% acrylamide gels (SDS-PAGE), as described by Laemnmli [Laemmli V. K. Nature 227:680–685, (1970)].

Amino Acid Sequencing

Sequencing was carried out at the Bletterman Marcromolecular Research Laboratory of the Hebrew University in the Interdepartmental Equipment Unit of the Faculty of Medicine. Sequences were determined on a Perkin-Elmer Applied Biosystems Division model 429 Precise Microsequencer System.

Depletion of Plasma IgG

Plasma (5 ml) were incubated with 1 ml of IgG (bound to beads, as described) for 2 hr, at 4° C. The beads were precipitated by centrifugation and the plasma was decanted and used for precipitation of radiolabeled suPAR or for formation of clots after addition of thrombin, as described herein before.

Interaction Between SuPAR and IgG

Binding of $^{125}$I-suPAR to IgG was determined by incubation of 50 nM radiolabeled suPAR, 0.1 ml plasma and 0.5 ml of IgG protein, for 2 hr at 4° C. Following incubation, the mixture was centrifugated. The precipitate was washed 4 is times with PBS and the radioactivity incorporated into protein G was determined. Non-specific binding was determined by using plasma that had been depleted of IgG or by measuring the precipitation of irrelevant protein. All experiments were repeated at least three times.

Example 4
The effect of SuPAR of ScuPA Mediated Fibrinolysis

Figure 1B:
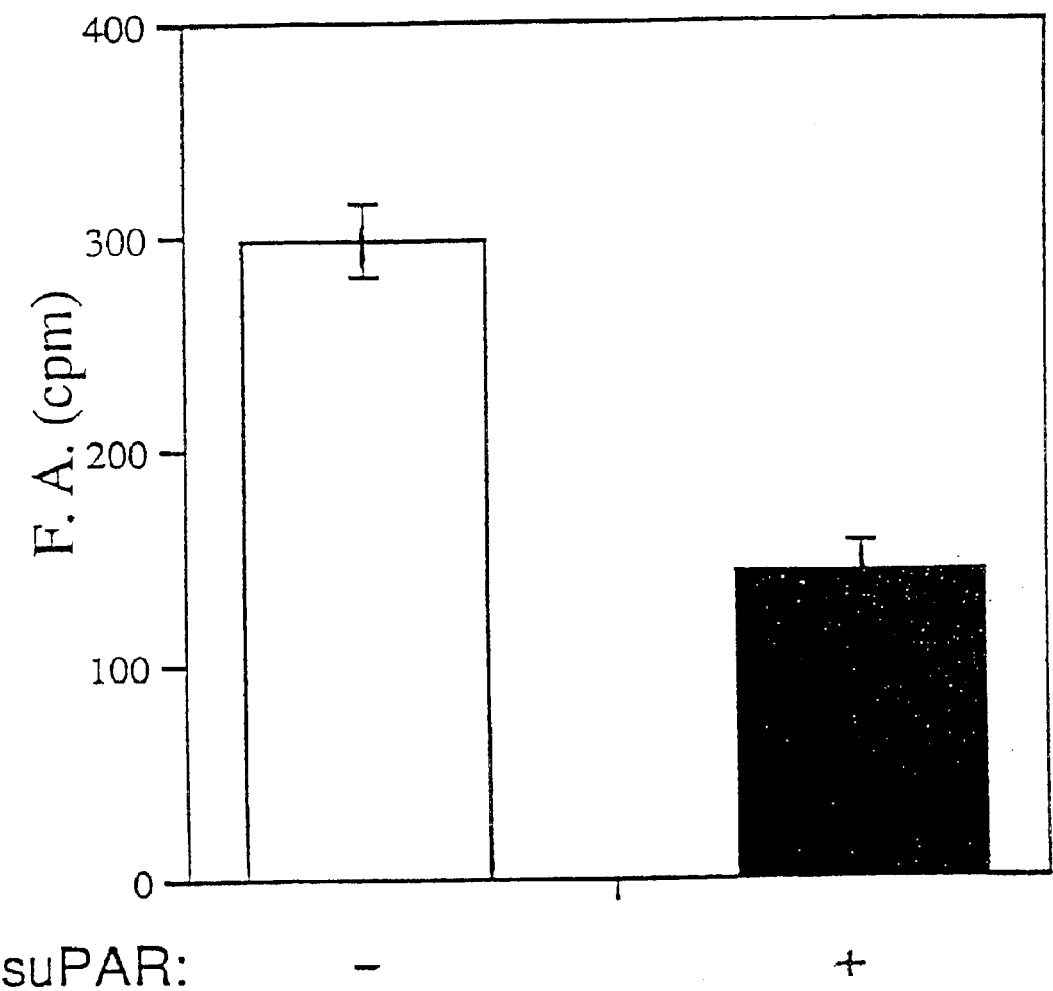
Figure 2A:
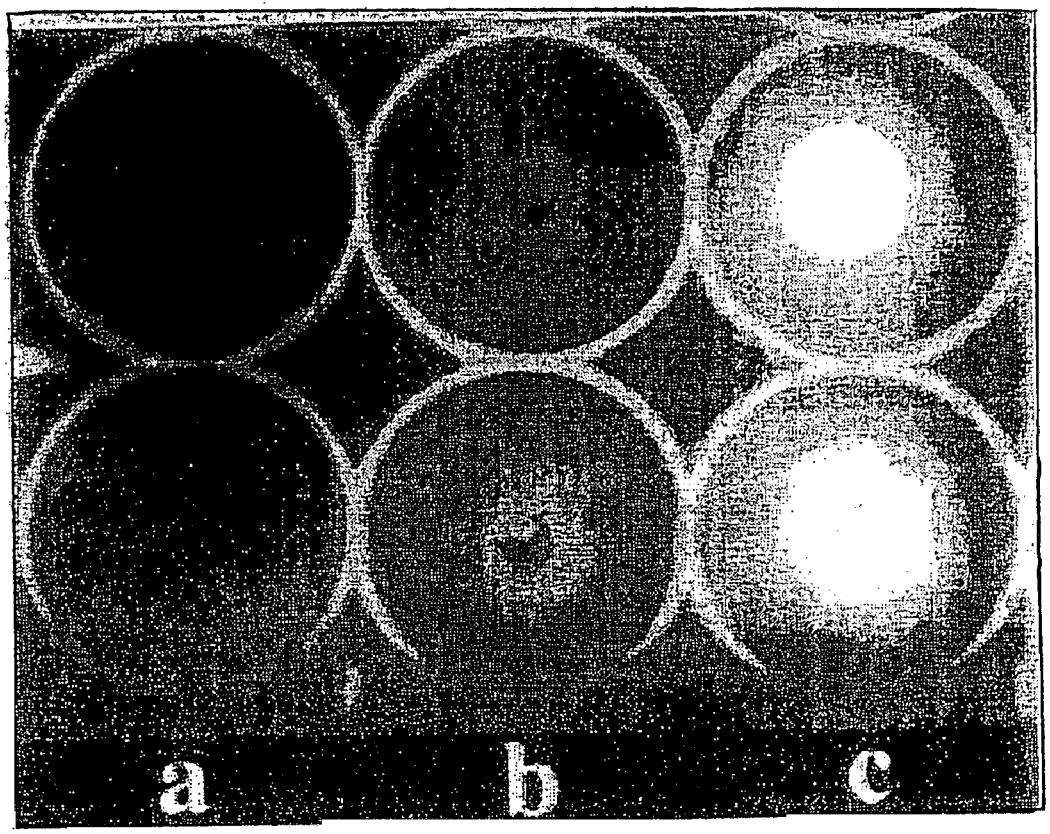
FIG. 2 The effect of suP AR on scuPA mediated fibrinolysis (human plasma clot)
(A) Lane (a)—suPAR alone; lane (b)—scuPA alone; and lane (c)—scuPA and suPAR. The size of the lytic area in (c) was 0.94 and 0.90 $cm^2$, in the upper and lower panels, respectively.
(B) ScuPA (open bar) or scuPA/suPAR complex (closed bar) were added to $^{125}I$ radiolabeled fibrinogen clots. After 2 hrs of incubation the fibrinolytic activity (FA. (cpm)) was determined by measuring the solubilized radioactivity.
Figure 2B:
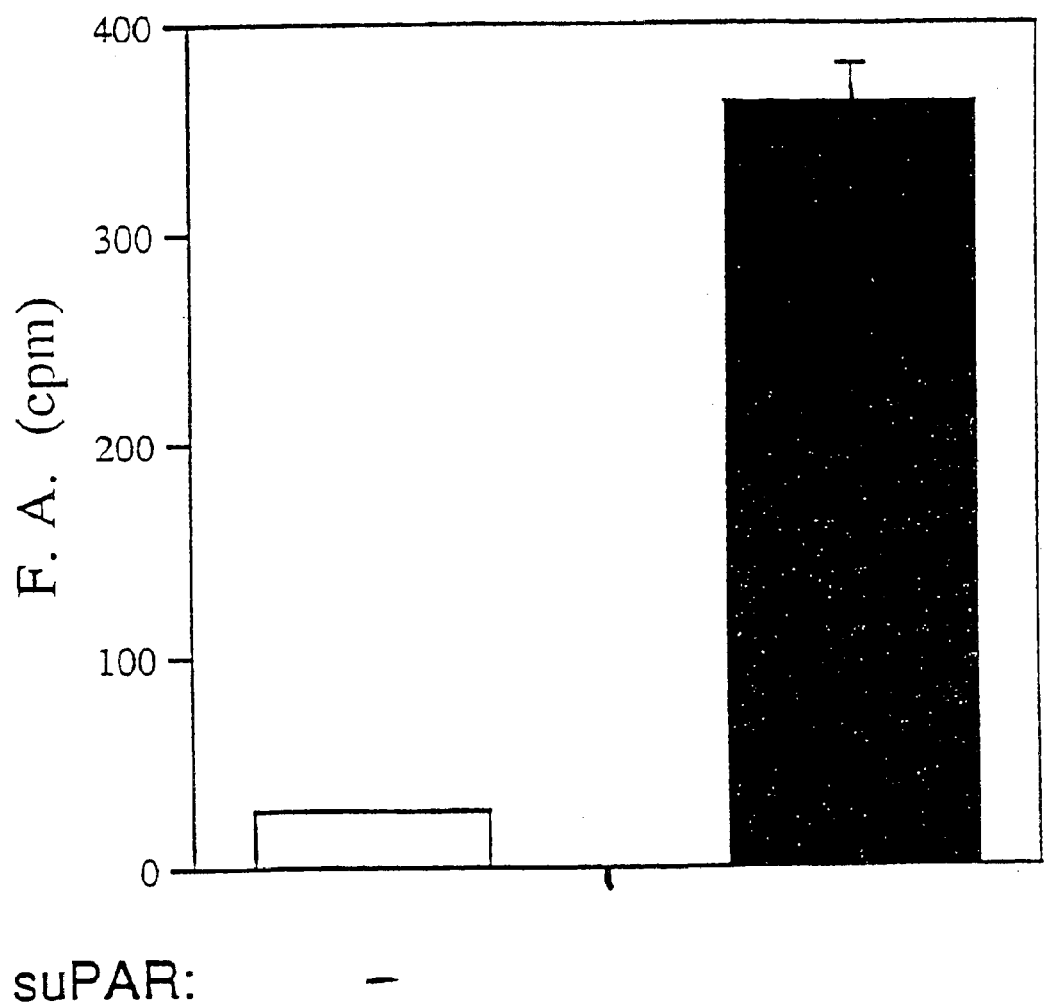

Fibrin generated by the incubation of thrombin with unlabeled bovine fibrinogen FIG. 1(a)) or radiolabeled fibrinogen (FIG. 1(b)) was used as the substrate of the fibrinolytic system. In the presence of suPAR the activity of scuPA in the two systems was inhibited by about 40% and 50%, respectively. The effect of suPAR under these conditions was similar to that previously obtained with S-225 1 as substrate [Higazi A A-R. (1997) ibid.]. In an attempt to identify physiological conditions that would enhance scuPA's activity, like that previously observed with the synthetic substrate Spect PL [Higazi A A-R. et al. (1995) ibid.; Higazi A A-R. et al. (1996) ibid.; Higazi A A-R & Cines D. B. (1996) ibid.], the effect of suPAR on scuPA activity with clots formed by the addition of thrombin to unlabeled (FIG. 2(a)) or radiolabeled plasma (FIG. 2(b)) was examined. ScuPA activity on these clots was less than 10% of that on purified fibrinogen clots (see FIGS. 1(a) and 1(b)), whereas addition of suPAR induced up to 14 fold enhancement of scuPA-mediated fibrinolysis (FIG. 2). It was therefore concluded that with the physiological substrate of the fibrinolytic system, uPAR can regulate the activity of scuPA.

The effect of ATF on suPAR -induced Stimulation of Fibrinolysis

To exclude the possibility that the stimulatory effect of suPAR was due to cleavage and activation of scuPA by contanainating proteases, or by an effect of suPAR on other elements of the fibrinolytic system, two control experiments were carried out.

Figure 3A:
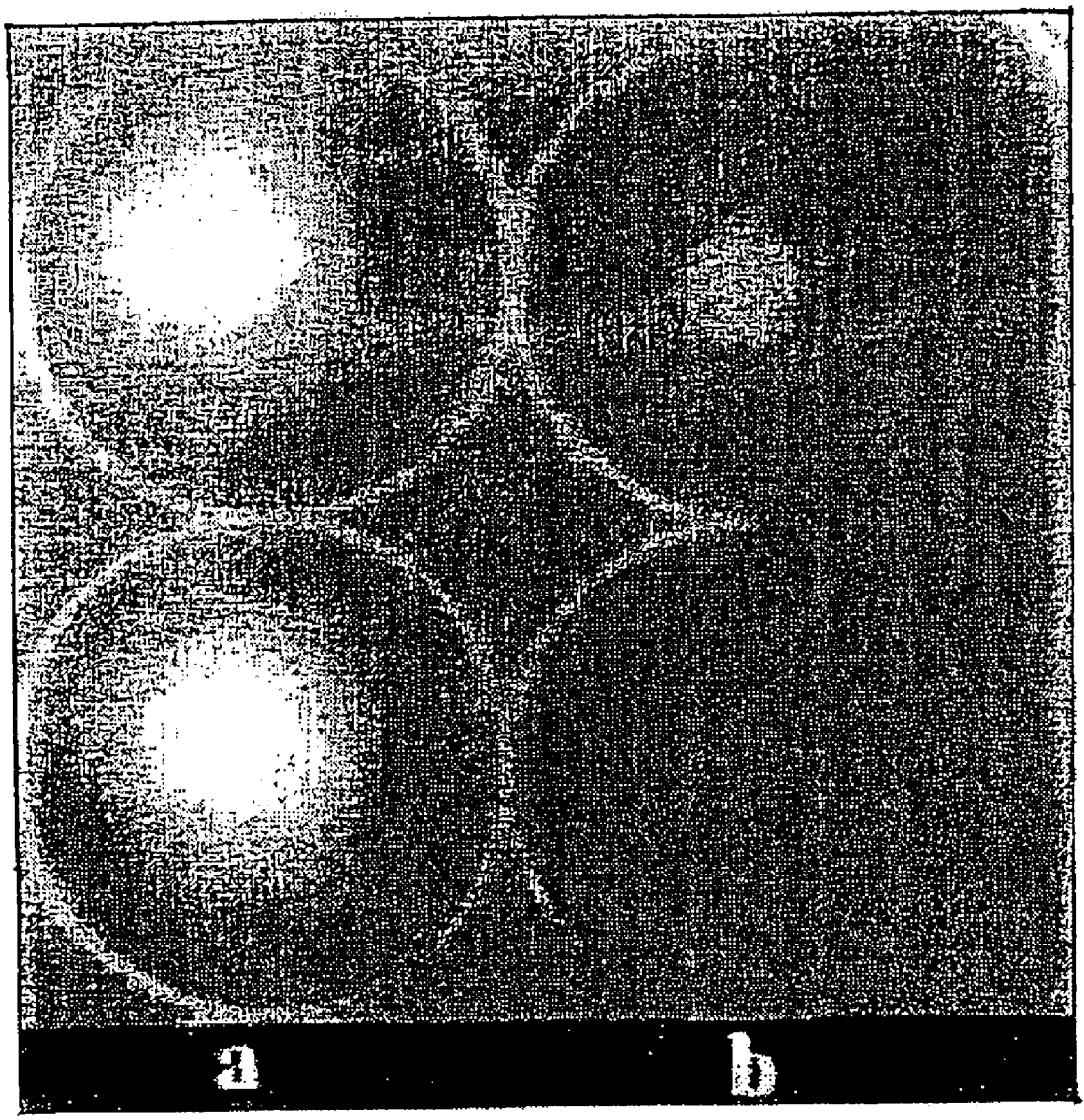
FIG. 3 The effect of the amino-terminal fragment of urokinase (ATF) on suPAR-induced stimulation of fibrinolysis (plasma clot)
(A) Lane (a) scuPA and suPAR, lane (b) scuPA, suPAR and ATF.
(B) ScuPA/suPAR complex without (open bar) or with ATF (black bar) added to $^{125}I$-radiolabeled fibrinogen clots. After 2 hrs of incubation the fibrinolytic activity (F.A (cpm)) was determined by measuring the solubilized radioactivity.
Figure 3B:
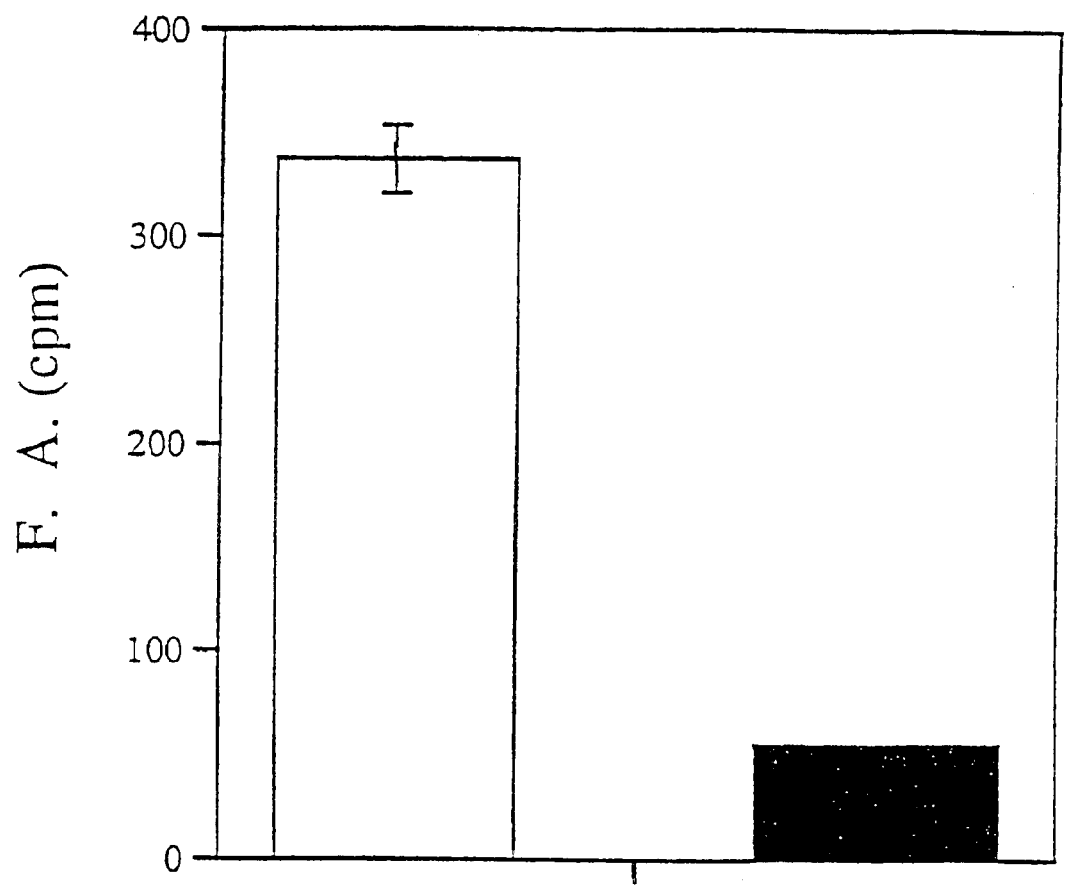

Blocking of the interaction of scuPA with suPAR by ATF, caused an almost complete inhibition of the stimulatory effect of suPAR on scuPA-mediated fibrinolysis (FIGS. 3(a) and 3(b)). Furthermore, LMW-scuPA, that cannot interact with suPAR because of the absence of ATF, was not affected by the presence of suPAR (FIG. 4).

It was therefore concluded that suPAR has a stimulatory effect on scuPA activity on clots formed by human plasma, whereas it inhibits fibrinolysis of clots formed by purified bovine fibrinogen. The possibility that the different effects are related to the source of fibrinogen, human or bovine, was examined. The inhibition of scuPA activity observed with bovine fibrinogen (FIG. 1), was also observed when human fibrinogen was used (not shown). It was then suggested that the plasma may contain a regulator for the activity of the scuPA/suPAR complex, and which is not present in a purified fibrinogen.

The Effect of suPAR on scuPA-mediated Fibrinolysis

Figure 5:
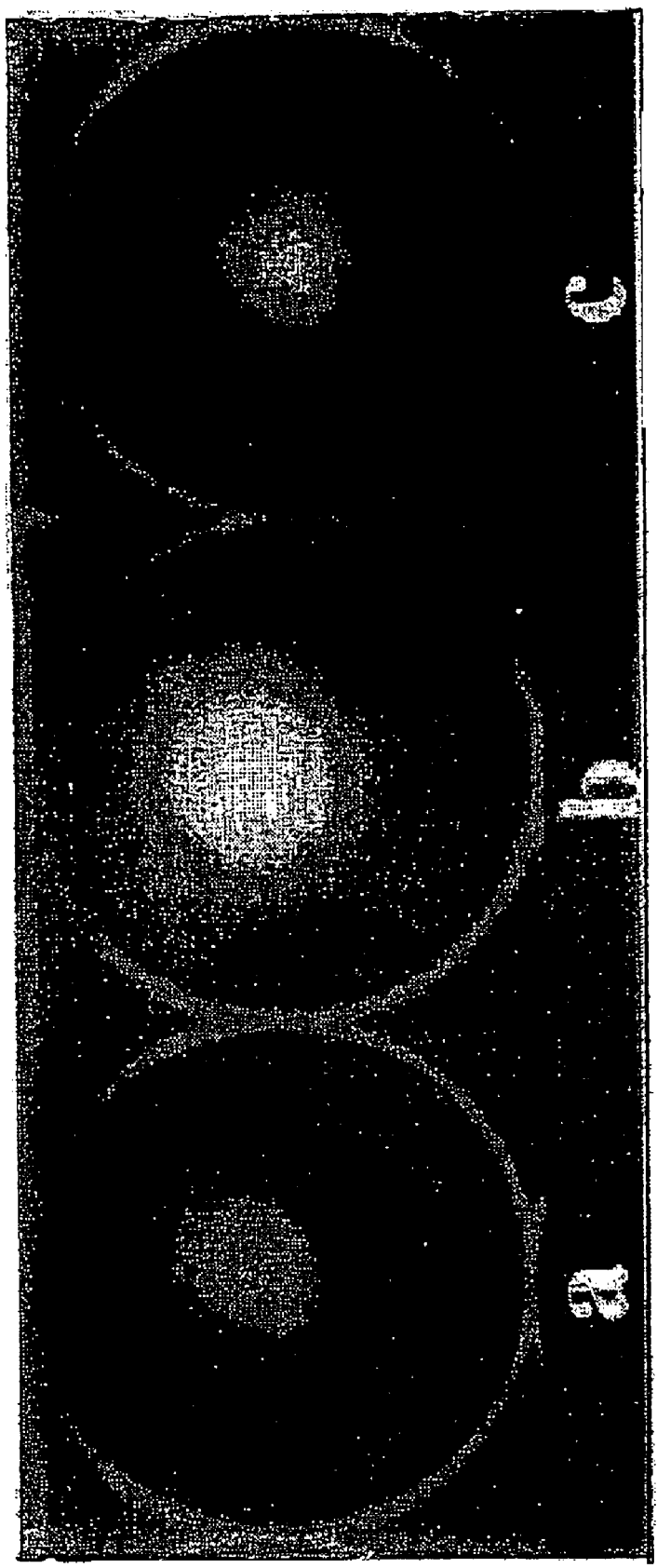

In an experiment designed to test the possibility that the different effects were related to the source of fibrinogen, the fibrinogen was removed from plasma by clotting with thrombin and removal of the clot by centrifugation to obtain serum. Addition to the serum of purified bovine fibrinogen, followed by thrombin, resulted in formation of a clot that was cleaved by the scuPA/suPAR complex with greater efficiency than by scuPA alone, a pattern similar to the cleavage of the clot originally formed from human plasma (FIG. 5). In addition, it seems that the stimulatory effect of suPAR under these conditions can be abolished by ATF. The possibility that the stimulatory activity was derived from the anticoagulants present in plasma was considered. Addition of CPD solution to a clot formed by fibrinogen had no stimulatory effect on scuPA and had an inhibitory effect on scuPA/suPAR mediated fibrinolysis (not shown).

The Effect of suPAR on scuPA Activity on a Plasma Derived Clot

To further examine the effect of suPAR on scuPA activity and the role of serum, the inventor set other systems in which the plasminogen activator(s) and the serum would be located in different compartments. For example, the effect of suPAR on scuPA mediated plasminogen activation as occurring on the clot surface was also examined.

FIG. 6 shows that suPAR stimulates the activity of scuPA on a plasma clot even when both were added to serum that covered the clot, rather than directly to the clot surface, (as shown in FIG. 2). In this system half maximal fibrinolysis was achieved at 54 min. by the scuPA/suPAR complex, in contrast to 210 min required with scuPA alone (FIG. 6(b)). The scuPA/suPAR mediated fibrinolysis was dose-dependent, and doubling the concentration of the complex resulted in a decrease of the time needed for half maximal fibrinolysis to 33 min., whereas a 50% decrease of the concentration of the complex resulted in half maximal fibrinolysis at 102 min. (data not shown). FIG. 6 also shows that the addition of 250 nM ATF significantly inhibited scuPA/suPAR mediated-fibrinolysis and that the effect of suPAR on fibrinolysis depends on the presence of scuPA. SuPAR fragments that contain DI or DII–DIII can bind to scuPA and stimulate its activity on a small plasmin substrate [Higazi A A-R er al. (1997) ibid.]. Neither of these fragments, nor combinations of the same, stimulated scuPA activity in the described system (not shown), and it was thus concluded that the intact suPAR is required for stimulation of scuPA. To determine whether the stimulation of fibrinolysis could be elicited when serum was present only in the clot or if it has to be present in the liquid phase as well, The effect of suPAR on scuPA activity a plasma-derived clot covered with PBS instead of serum was examined. FIG. 6 shows that the fibrinolytic activity of the scuPA/suPAR complex on a plasma clot was not affected by the presence of PBS. instead of serum, on the surface of the clot. With scuPA alone, rather than the scuPA suPAR complex the fibrinolytic activity was greater in clots covered by PBS than by serum (FIG. 6(a)). The time to achieve half maximal fibrinolysis was reduced by 25% in PBS. compared to serum (FIG. 6(b)). Evidently, plasma derived clots covered with plasma instead of serum, exhibited the same effect (data not shouts). thus leading to the conclusion that the putative regulator is present in the plasma as well as in the serum.

The Effect of SuPAR on ScuPA Activity on a Fibrinogen Derived Clot

Naturally, also the opposite situation was questioned, such as whether the presence of serum only in the medium covering the clot, but not in the clot itself, would be sufficient to induce stimulation of the scuPA/suPAR complex. To this end a clot formed by purified fibrin was covered with serum or PBS. The presence of serum stimulated fibrinolysis by the scuPA/suPAR complex (FIG. 7), but the fibrinolytic activity of the scuPA/suPAR complex was only about 60% of that obtained on a plasma-derived clot (FIGS. 7(b) and 6(b)). However, in contrast to the scuPA/suPAR complex in which serum enhanced the rate of fibrinolysis, with scuPA alone the rate of fibrinolysis was decreased in the presence of serum (FIG. 7), similar to the effect of plasma on scuPA-mediated fibrinolysis described by Lijnen et al. [Lijnen, H. R, Blood 73:186–1872 (1989)]. FIG. 7 also reveals that the activity of scuPA alone on a fibrinogen-derived clot was greater than the activity of the scuPA/ suPAR complex in the same system; these results are consistent with the results presented in FIG. 1.

Comparison of Fibrinolysis Mediated by tcuPA and by scuPA/suPAR Complex

The fibrinolytic activity of the scuPA/suPAR complex was compared to that of tcuPA. Presented in FIG. 8 is the activity of tcuPA on a clot formed from purified fibrinogen and having PBS in the liquid phase which is greater than that of the scuPA/suPAR complex in the same system (see for comparison also FIG. 7). However, when the clot was formed by clotting of plasma the activity of the scuPA/suPAR complex was greater than that of tcuPA. The change in the ratio of activities with scuPA/suPAR and tcuPA is due to an increase in the activity of the complex as well as to inhibition of tcuPA activity when a plasma clot is used instead of a fibrinogen clot. The addition of suPAR to tcuPA had a small stimulatory effect, which may be due to a to decrease in its susceptibility to inhibition by PAI-1 [Ellis V. et al. (1990) ibid.].

Example 5
Determination of the Presence of a Regulator

Figure 9:
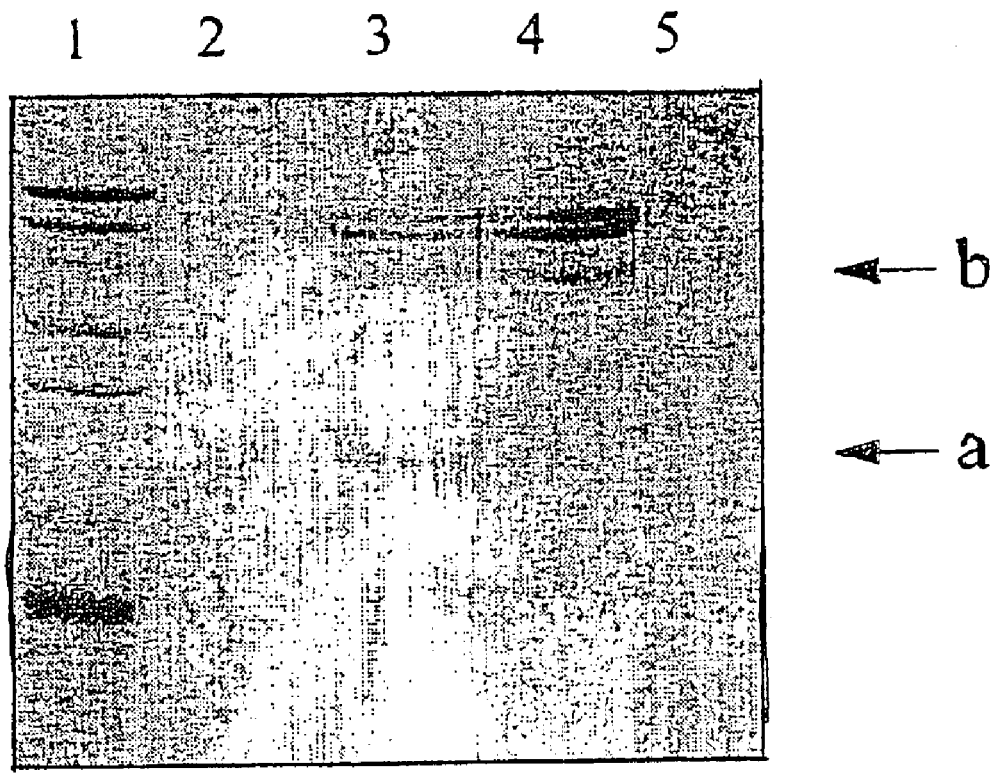
FIG. 9 SDS-PAGE analysis of the proteins bound to suPAR-Sephadex
Lane (1) molecular weight markers; lane (2) suPAR Sephadex incubated with PBS; lane (3) suPAR-Sephadex incubated with plasma; lane (4) suPAR-Sephadex incubated with scuPA and plasma; lane (5) suPAR-Sephadex incubated with scuPA and PBS.

The data presented herein before demonstrates that the plasma-derived clot is a better substrate for the scuPA/suPAR complex than for the scuPA or tcuPA mediated fibrinolysis. Therefore, it was postulated by the inventor that there is a factor, present in the plasma, that stimulates the activity of the complex. This tentative assumption is supported by the observation that in a partially purified system the complex is active only in the presence of certain regulators, such as Spect-PL [Higazi, A A-R. & Cines, D.E. (1996), ibid.; Wang, G. et al. Eur. J. Biochem. 247:256–261 (1997)]. To further examine this possibility, an affinity chromatography with Sepharose-bound suPAR was prepared. FIG. 9 presents the SDS-PAGE analysis, after incubating the suPAR-Sepharose with different substrates. When incubation in the presence of plasma (lane 3), or in the presence of scuPA(lane 4) was carried out, four bands were obtained from the precipitates. Similar bands were not obtained when incubation was performed in the absence of plasma (lanes 2 and 5). These results were repetitive for plasma obtained from four different donors.

The samples analyzed by SDS-PAGE, were further examined for their fibrinolytic activity, in order to verify that the ligands bound to the suPAR Sepharose contain the putative activity regulator of scuPA/suPAR complex. FIG. 10 shows that the scuPA/suPAR-mediated fibrinolytic activity on a fibrinogen derived clot, was significantly increased in the presence of plasma-derived proteins(s). Further, FIG. 10 exhibits that in the absence of such plasma-derived protein (s), the scuPA/suPAR complex had little fibrinolytic activity on the clot.

Identification of the Regulator

To further identify the regulator, the inventor has performed and amino-terminal sequence analysis of the two fastest migrating bands, presented in FIG. 9. The sequence of these two proteins was found to be EIVMTQPXTLS (SEQ ID NO:1) and EVQLVESGGXLVQPGRES(SEQ ID NO:3), respectively. Computer analysis of these sequences revealed identity with parts of the human IG protein, i.e. with human IG kappa V-III region (KV3F), which is part of the variable region of the light chain, and with human IG heavy chain V-III (HV3T), respectively.

The following is the comparison between the sequences of the proteins presented in lanes (a) and (b) in FIG. 9 and with the above identified segments of human IG protein:
Band (a) sequence EIVMTQSPXTLS(SEQ ID NO:1)
KV3F human sequence EIMTQSPVTLSVSPGERAT(SEQ ID NO:4)
Band (b) sequence EVQLVESGGXLVQPGXS(SEQ ID NO:2)
HV3T human sequence EVQLVESGGDLVQPGRSLRL (SEQ ID NO:5)

Figure 11:
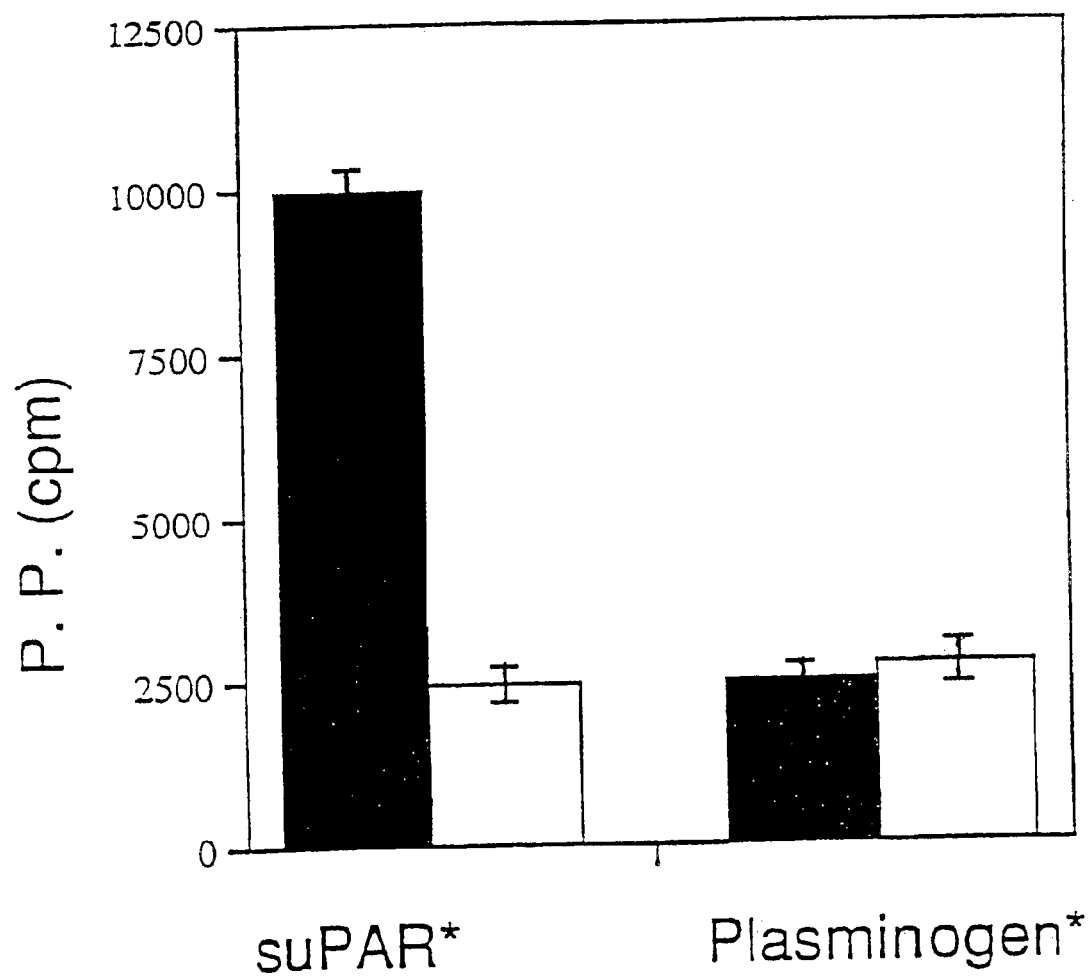
FIG. 11 Binding of suPAR to plasma IgG
$^{125}I$-suPAR or $^{125}I$-plasminogen at a final concentration of 50 nM were added, separately, to 0.5 ml of native plasma (closed bars) or to IgG-depleted plasma (open bars) followed by incubation with 0.5 ml protein G, as described herein after. Radioactivity incorporated into the precipitated protein (P.P. (cpm)) was determined.
Figure 12:
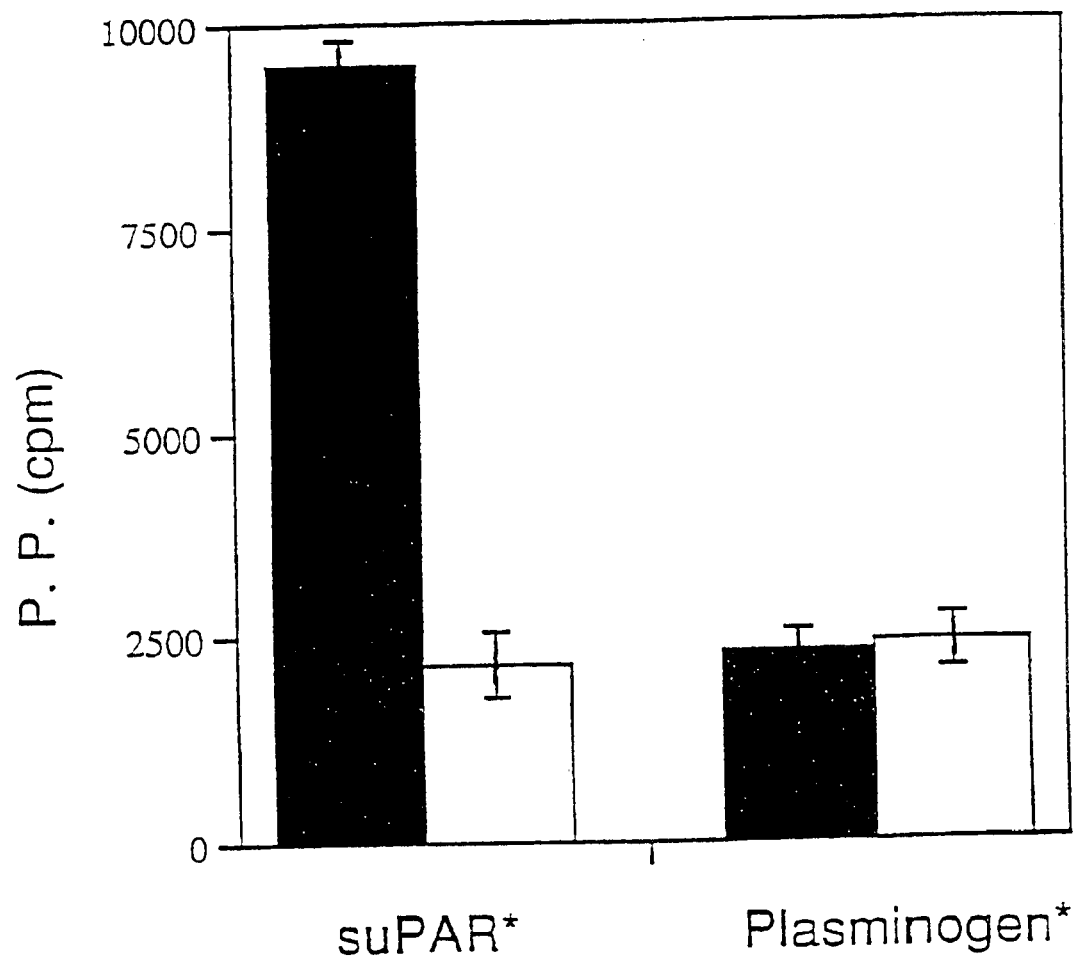
FIG. 12 Binding of suPAR to purified human IgG
Protein G was added to a mixture containing $^{125}I$-suPAR or $^{125}I$-plasminogen and IgG (closed bars) or BSA (open bars) as described herein after and the radioactivity incorporated into IgG (P.P. (cpm)) was determined.

In order to determine whether a similar interaction between IgG and suPAR occurs also in the plasma environment, radiolabeled suPAR or radiolabeled plasminogen were added to native plasma or to IgG depleted plasma, each followed by incubation with protein G. The results shown in FIG. 11 indicate that protein G immunoprecipitates suPAR from plasma, whereas under the same conditions. radiolabeled plasminogen was not precipitated by protein G. When the same experiment was performed with IgG-depleted plasma, precipitation of suPAR was reduced to less than 25%. When serum or IgG-depleted serum was used instead of plasma or IgG depleted plasma, similar results were obtained (data not shown). Furthermore, when purified human IgG was used instead of plasma, the same results were obtained as presented in FIG. 12. However, no interaction between IgG and suPAR was obtained when rabbit serum was used instead of human serum (data not shown).

Figure 13:
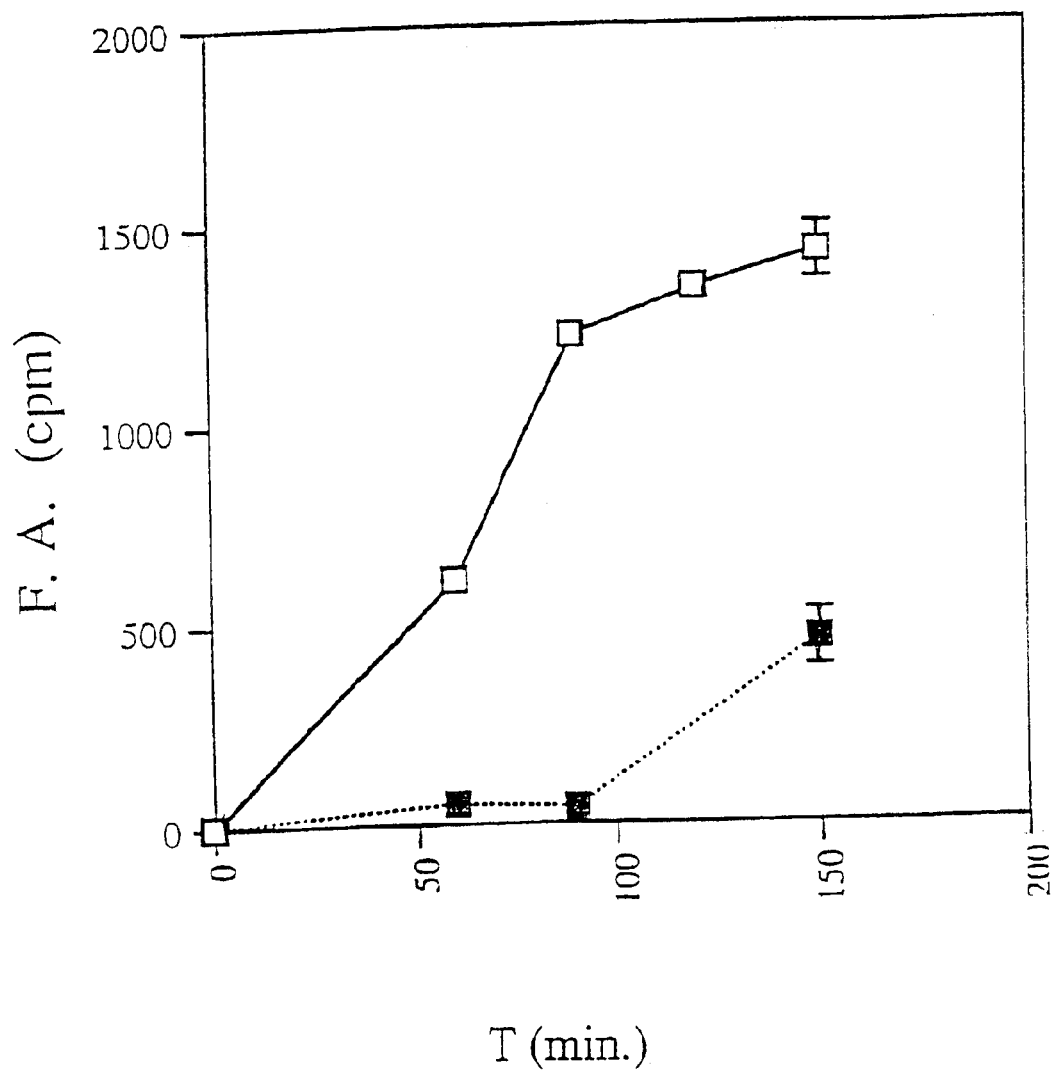
FIG. 13 The effect of IgG on lysis of a plasma-derived clot scuPA/suPAR complex was added to clots formed by the addition of thrombin to native plasma (open symbols) or to IgG-depleted plasma (closed symbols). Fibrinolysis (F.A. (cpm)) was determined as described for FIG. 6.

Finally, the link between scuPA/suPAR mediated fibrinolytic activity and IgG was examined by measuring the rate of lysis of clots derived from normal or IgG depleted plasma. FIG. 13 shows that the scuPA/suPAR mediated fibrinolysis of a clot prepared from IgG-depleted plasma was markedly retarded.

What is claimed is:

1. A method of inducing fibrinolysis of plasma derived clots, said method comprising contacting the clot with a complex comprising a single chain urokinase plasminogen activator and a soluble urokinase plasminogen activator receptor in the presence IgG or an IgG-derived peptide, selected from the group consisting of SEQ ID NO.:1 and SEQ ID NO.:2, and, causing specific binding of the clot to the complex, thereby inducing fibrinolysis of the clot.

2. A method of regulating the thrombolytic activity of plasma derived clots comprising contacting the clot with a complex comprising a single chain urokinase plasminogen activator and a soluble urokinase plasminogen activator receptor in the presence of IgG, or IgG-derived peptide selected from the group consisting of SEQ ID NO.:1 which is the kappa V-III region of the light chain of human IgG and SEQ ID NO.:2 which is the V-III region of the heavy chain of human IgG, and causing specific binding of the clot to the complex, thereby regulating the thrombolytic activity.

3. A method of treating or preventing a thromboembolic disorder associated with the formation of fibrin clots, said method comprising administering a complex comprising a single chain urokinase type plasminogen activator receptor, wherein the complex has a thrombolytic activity under physiological conditions when in the presence of IgG or IgG-derived peptide selected from a group consisting of SEQ ID NO:1 which is the kappa V-III region of the light chain of human IgG, SEQ ID NO:2 which is the V-III region of the heavy chain of human IgG, and causing specific binding to the complex, thereby resulting in fibrinolysis of said clots.

4. The method of claim 3, wherein said complex has a fibrin-specific thrombolytic activity under physiological conditions.

5. The method of claim 3, wherein said disorder is selected from the group consisting of a myocardial infarction, a cerebro-vascular event, a pulmonary embolism and a deep vein thrombosis.

6. A composition comprising a complex of a single chain urokinase type plasminogen activator, a soluble urokinase type plasminogen activator receptor, and IgG derived peptides which are the kappa V-III region of the light chain of human IgG, and the V-III region of the heavy chain of human IgG.

7. The composition of claim 6 wherein the IgG-derived peptide, the kappa V-III region of the light chain of human IgG is SEQ ID NO:1 and the IgG-derived peptide, the V-III region of the heavy chain of human IgG is SEQ ID NO:2 as identified by SDS-PAGE analysis using molecular markers.

8. The composition of claim 6, optionally further comprising one or more of the components including a pharmaceutically acceptable carrier, adjuvant or preserving agent.

9. A method of treating or preventing a thromboembolic disorder associated with the formation of fibrin clots by administering an effective amount of a composition according to claim 6, wherein the amount used is sufficient to induce fibrinolysis of said fibrin clots.

10. The method according to claim 9, wherein the thromboembolic disorders include myocardial infarctions, cerebrovascular events, pulmonary embolism or deep vein thrombosis.

11. The method of claim 9, wherein said disorder is selected from the group consisting of myocardial infarction, cerebrovascular event, pulmonary embolism and deep vein thrombosis.

12. A composition comprising a complex of a single chain urokinase type plasminogen activator, a soluble urokinase type plasminogen activator receptor, and IgG derived peptides which are the kappa V-III region of the light chain of human IgG, and the V-III region of the heavy chain of human IgG, said composition produced by:

incubating the single chain urokinase type plasminogen activator (scuPA) with the soluble urokinase type plasminogen activator receptor (suPAR) on sepharose beads for 1 hr at 4° C. to produce a scuPA-suPAR complex, adding citrated plasma containing IgG to the scuPA-suPAR complex and incubating for 1 hr at 4° C.; and isolating and washing the scuPA-suPAR-IgG complex by centrifuging the complex.

* * * * *